United States Patent [19]

Kausek et al.

[11] Patent Number: 4,732,143
[45] Date of Patent: Mar. 22, 1988

[54] SELECTABLE EXTENSION STOP FOR A POLYCENTRIC HINGE

[75] Inventors: James Kausek, Swampscott; Al Klugman, Waban, both of Mass.

[73] Assignee: Spectrum Orthopedics, Ltd., Boston, Mass.

[21] Appl. No.: 14,357

[22] Filed: Feb. 13, 1987

[51] Int. Cl.⁴ ............................................. A61F 5/00
[52] U.S. Cl. ................................... 128/80 C; 128/88; 128/80 F
[58] Field of Search .................... 128/80, 80 C, 80 H, 128/80 E, 80 F, 80 G, 80 A, 80 B, 80 D, 88

[56] References Cited

U.S. PATENT DOCUMENTS

| | | | |
|---|---|---|---|
| 3,902,482 | 9/1975 | Taylor | 128/80 F |
| 3,923,047 | 12/1975 | Chaut | 128/88 |
| 4,088,130 | 5/1978 | Applegate | 128/80 F |
| 4,493,316 | 1/1985 | Reed et al. | 128/80 C |
| 4,520,804 | 6/1985 | Di George | 128/80 C |
| 4,599,998 | 7/1986 | Castillo | 128/80 C |
| 4,633,867 | 1/1987 | Kausek et al. | 128/88 |

Primary Examiner—Edgar S. Burr
Assistant Examiner—Huong Q. Pham
Attorney, Agent, or Firm—Wolf, Greenfield & Sacks

[57] ABSTRACT

An extension stop removably mountable on a polycentric hinge for limiting the forward pivotal rotation of a pair of rigid arms pivotally connected by the hinge. The hinge is of the type wherein a pair of rigid arms are connected at spaced-apart pivotal connections between a pair of parallel face plates. Intermeshing gear teeth are provided on the mating ends of the arms so as to cause simultaneous pivotal action of both arms about their pivotal connections with the plates. The extension stop is a C-shaped plastic body which is attachable along one of the face plates. The stop includes a resilient clip for attaching the stop to one of the face plates and an extension block at the opposing end positionable between the mating ends of the arms to limit the forward rotation of the arms. The extension stop is made of a strong, lightweight plastic. Different size block means are provided to allow the user to select the limit of extension.

9 Claims, 9 Drawing Figures

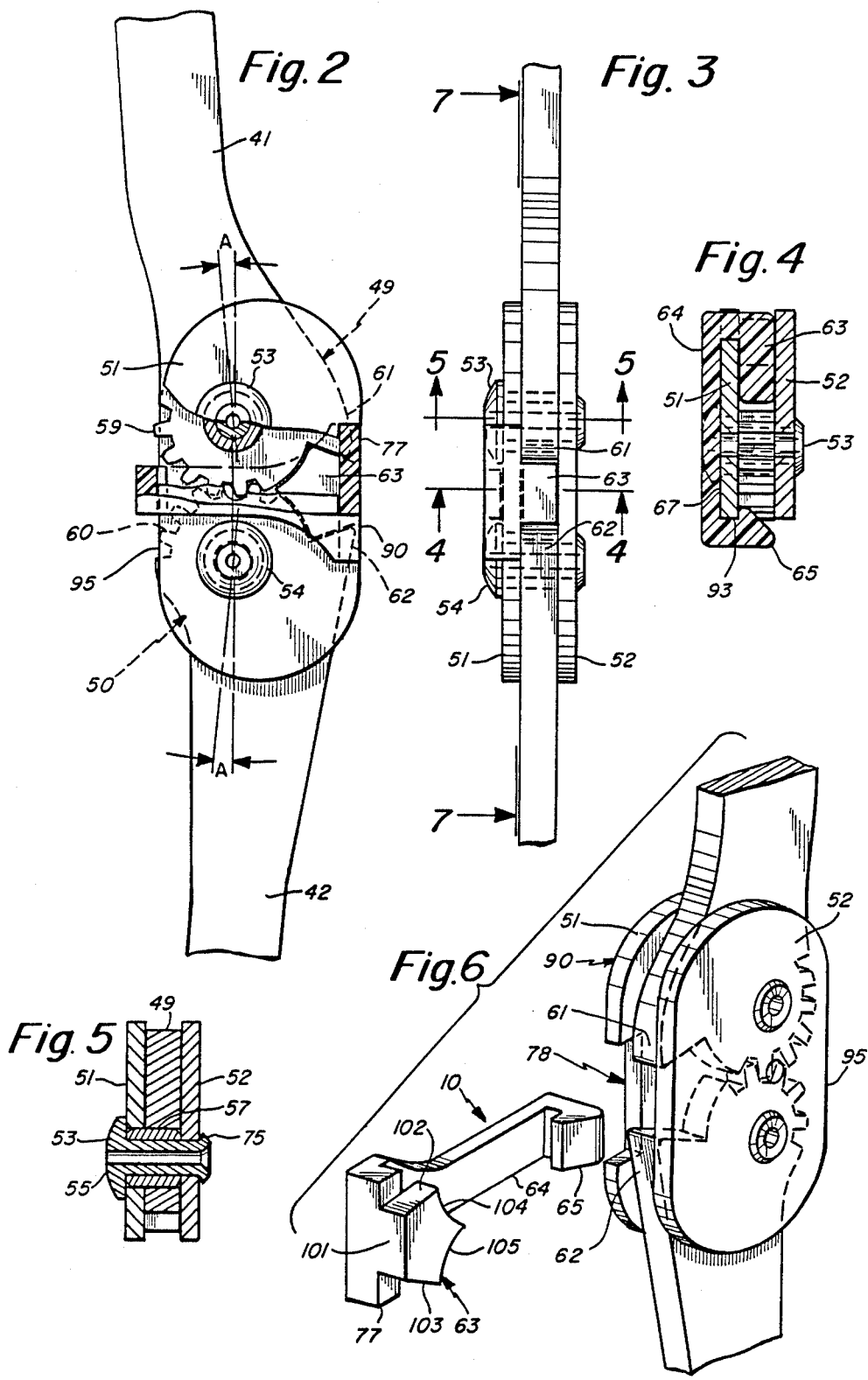

SELECTABLE EXTENSION STOP FOR A POLYCENTRIC HINGE

BACKGROUND OF THE INVENTION

This invention relates to a polycentric hinge for a knee brace or other hinged device, and more particularly to a selectable extension stop for limiting the pivotal movement allowed by the hinge.

When the ligaments surrounding the knee have been traumatized by injury or by surgery, a supporting brace is used which permits controlled pivotal movement of the knee elements to restore their strength and natural range of movement. The brace should protect the knee from lateral and rotational movements and prevent hyperextension of the knee beyond the point of natural articulation. For example, a known knee brace has shin and thigh plates and, extending down both the medial and lateral sides of the leg, a pair of rigid arms which are pivotally connected at the knee by a polycentric hinge. This brace allows the knee to bend but prevents lateral and rotational movements.

Additional knee brace elements have been suggested to prevent the knee from pivoting forwardly beyond a maximum desired articulation, i.e., hyperextending. It has been suggested to provide flexible straps connecting the arms or the shin and thigh plates to prevent a full unbending of the knee. Another brace includes a pair of notches on one of two pivotally connected hinge elements which notches cooperate with a fixed pin and a selectively positionable pin on the other element (U.S. Pat. No. 4,088,130 to Applegate). Another brace provides a fixed stop on a polycentric hinge which engages a pair of shoulders on the ends of two rigid arms having intermeshing gear teeth (U.S. Pat. No. 4,524,764 to Miller et al.). Still another brace provides a pinion stop gear which meshes with and is selectably rotatable about the periphery of each of the hinge gears of a polycentric hinge (U.S. Pat. No. 4,493,316 to Reed et al.). Yet another brace provides a pair of stop pins releasably insertable in the left and right portions of a groove in a bracket disposed adjacent a polycentric hinge (U.S. Pat. No. 4,337,764 to Lerman).

Each of these prior devices suffers from either a lack of adjustability, undue complexity, or a lack of stability. Therefore, it would be desirable to provide a polycentric hinge for a brace having a simple, adjustable and secure means for limiting the pivotal movement of the arms connected by the hinge.

SUMMARY OF THE INVENTION

According to this invention, a removable wedge extension stop is provided for limiting the forward pivotal movement of a pair of arms connected by a polycentric hinge. The extension stop is useful for a knee, elbow, or other type of brace or hinged device which includes a polycentric hinge where it is required to limit the pivotal movement allowed by the hinge.

The extension stop of this invention includes a means for removably attaching the stop to a polycentric hinge and an extension block limiting the forward pivotal movement of the arms connected by the hinge. The extension block is specially shaped to cooperate with a pair of complimentary shaped flanges on the ends of the arms to secure the stop in position. A plurality of stops are provided each having a different size extension block to selectively limit the rotation of the arms. Preferably, the stop is made of a strong, lighweight plastic and includes a resilient clip portion to permit removeable attachment of the stop to the hinge.

The stop is designed for use with a polycentric hinge of the type which includes a pair of parallel, spaced-apart face plates. A pair of upper and lower rigid arms are pivotally secured at one end between the face plates at spaced-apart pivotal connections. The ends of the arms adjacent the pivotal connections have intermeshing gear teeth which cause simultaneous pivotal movement of both arms about their pivotal connections with the plates. The ends of the arms adjacent the pivotal connections further include specially shaped flanges which cooperate with the extension block to limit the forward pivotal movement of the arms.

In the preferred embodiment, the extension stop comprises a C-shaped body positionable across one of the face plates of the polycentric hinge. The body includes a resilient hook or clip at one end for removable attachment to the rear edge of one of the face plates. By rear edge it is meant the edge adjacent the back of the leg. The body further includes an extension block adjacent the front edge of the hinge, i.e., facing the front of the leg or knee. A connecting member disposed along the outer surface of the one face plate extends between the extension block and clip.

The preferred extension block is a multi-sided block having a linear and vertically disposed front side adjacent the front of the hinge, and a pair of opposing top and bottom sides which diverge outwardly from front to rear. An outwardly projecting flange on the end of each arm is positioned to lie along the opposing top and bottom edges of the rotation block so as to exert a continual rearward force on the extension block to hold the block securely on the hinge.

Futhermore, in the preferred embodiment the mating ends of the arms are offset forwardly of the vertical center line of the arms so that the hinged arms better conform with the leg geometry.

BRIEF DESCRIPTION OF THE DRAWINGS

FIG. 2 is a side partially sectional view of the arms, polycentric hinge, and extension stop of this invention which allows a 170° extension of the arms.

FIG. 3 is front view of the arms, polycentric hin ge and extension stop of FIG. 2.

FIG. 4 is a cross sectional view taken along section lines 4—4 in FIG. 3 showing the C-shaped extension stop positioned on the hinge.

FIG. 5 is a cross sectional view taken along section lines 5—5 of FIG. 3 showing a pivotal connection of an arm and the hinge.

FIG. 6 is an exploded front perspective view, partially in section, of the arms, polycentric hinge and extension stop.

DETAILED DESCRIPTION OF THE PREFERRED EMBODIMENT

Figure 1:
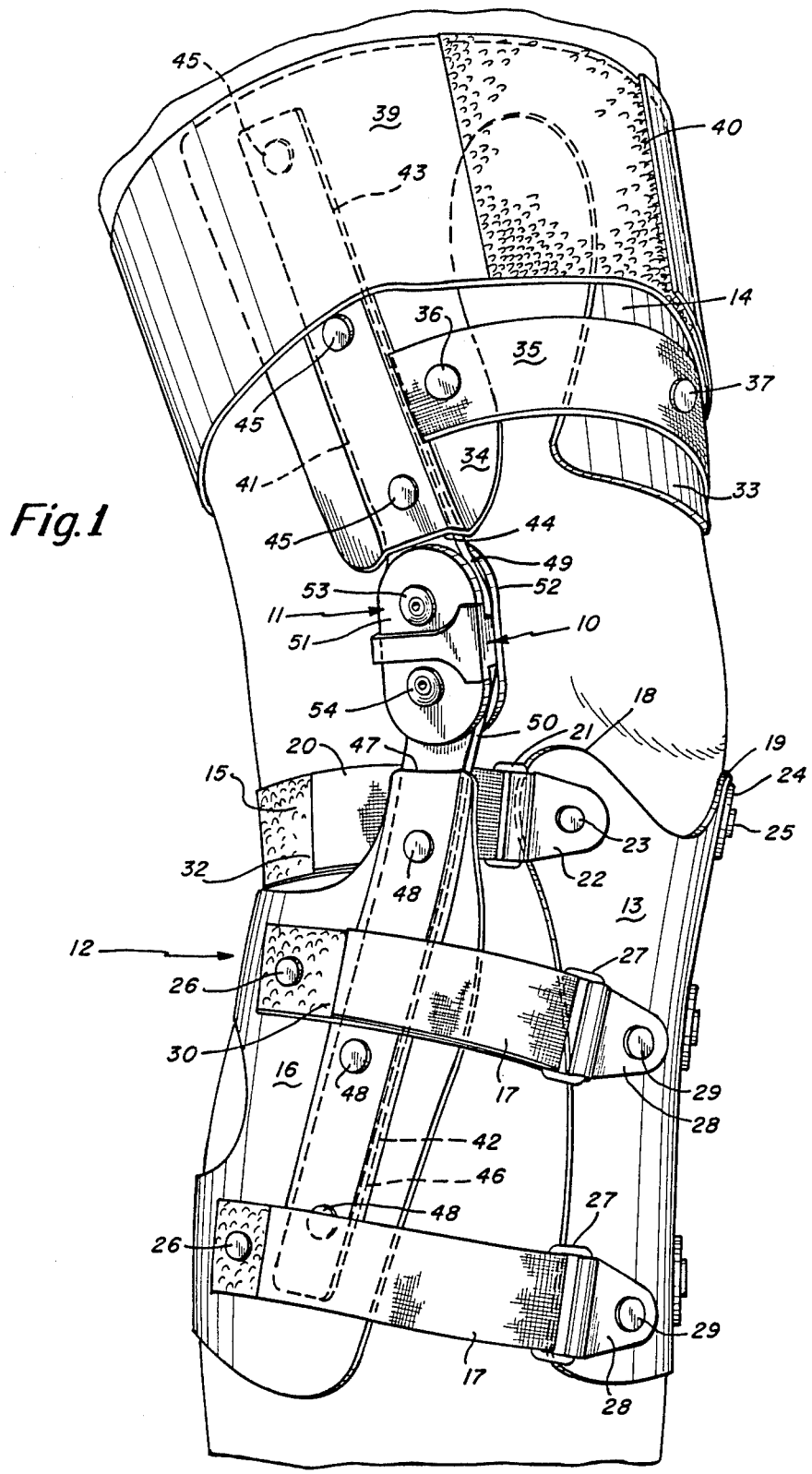
FIG. 1 is a persepctive view of a knee brace mounted on a leg, which brace includes a polycentric hinge and the extension stop of this invention.

A preferred embodiment of the removable wedge extension stop 10 of this invention is shown in FIG. 1 mounted on a polycentric hinge 11 of a knee brace 12. The knee brace shown in FIG. 1 is by way of example only and is more fully described in U.S. Pat. No. 4,633,867 to Kausek et al.

The knee brace includes a shin plate 13 shaped to fit over the front of the leg and extend from the knee downwardly over the skin. A thigh plate 14 is shaped to fit over the front of the leg and extend from the knee upwardly over the thigh. The shin plate 13 is secured to the leg by means of a flexible upper strap 15, a wide calf band 16, and a plurality of lower flexible straps 17 extending between the shin plate and calf band. Upper strap 15 extends around the back of the leg and is adjustably attached by passing one end 20 through a metal ring 21 (secured by a plastic tab 22 and metal rivet 23 to the shin plate 13) and securing the one end 20 to another portion of strap 15 with Velcro type attachment means 32. The opposing end 24 of the upper strap is permanently attached to the medial side edge 19 of the shin plate by a rivet 25.

The flexible calf band 16 is wrapped around the back of the leg in the middle of the calf. The lower straps 17 extend between the calf band 16 and shin plate 13 on the lateral and medial sides of the legs. A rivet 26 permanently attaches one end of each strap 17 to the calf band. The other end of each strap 17 is removably and adjustably attached to the shin plate by a metal ring 27, platic tab 28, rivet 29 and is secured by Velcro type attachment means 30 (similar to the attachment of upper strap 15).

The thigh plate 14 includes a suprapatellar flange 33 on the front of the thigh and two lateral side projections 34 on opposing sides of the leg. A tensioned suprapatellar band 35 is attached at opposing ends to the opposing side projections by rivets 36 and is attached to a central point of the suprapatellar flange by a rivet 37, for preventing the brace from sliding down the leg. A wide elastic thigh strap 39 is wrapped around the middle of the thigh over the thigh plate and is adjustably and removably secured at opposing ends by Velcro type attachment means 40.

As shown in FIG. 1, at the lateral (outer) side of the leg, a rigid upper arm 41 extends downwardly from the thigh plate and a rigid lower arm 42 extends upwardly from the calf band. The upper end 43 of the upper arm 41 is disposed within a pocket 44 in side projection 34 of the thigh plate and is secured thereto by three spaced rivets 45. The lower end 46 of the lower arm 42 is similarly disposed in a pocket 47 in the calf band 16 and is secured thereto by three spaced rivets 48.

Arms 41 and 42 are connected at mating ends 49 and 50 by a polycentric hinge 11. An identical pair of rigid upper and lower arms and hinge are provided on the medial (inner) side of the leg (not shown). These opposing pairs of arms prevent lateral (i.e., side-to-side) and rotational or twisting movement of the knee.

The mating ends 49 and 50 of the upper and lower arms, respectively, are disposed between a pair of parallel spaced-apart face plates 51, 52 of the polycentric hinge 11. The mating ends 49, 50 are pivotally secured to the face plates at spacedapart pivotal connections by means of rivets 53, 54 which extend through aligned apertures in the face plates and the mating ends (see FIG. 5). The rivets have shouldered heads 55, 56 and pass through brass bushings 57, 58 which permit the mating ends 49, 50 to pivot about the connections. The rivets are peened over at their far ends 75, 76 on the outside of plate 52.

The mating ends 49, 50 of the arms further include gear teeth 59, 60 adjacent the rear edge 95 of the hinge. Gear teeth 59 and 60 mesh with one another so as to cause simultaneous pivotal movement of the arms about their pivotal connections with the plates.

Figure 7:
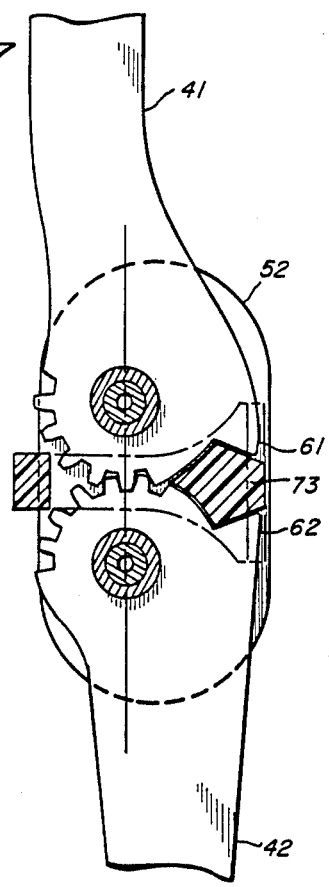
FIG. 7 is a side partially sectional view taken along section lines 7—7 of FIG. 3 of an extenstion stop which allows a 180° extension of the arms.
Figure 9:
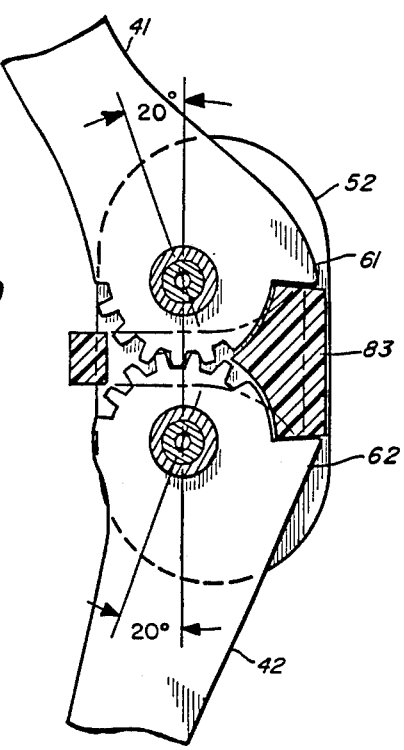
FIG. 9 is a side partially sectional view of the hinge and a stop which allows a 100° extension of the arms.

As shown in FIGS. 2, 7 and 9, flanges 61, 62 are provided adjacent the front edge 90 of the hinge 11. By front edge of the hinge it is meant the edge of the hinge facing the front of the leg or the knee. The flanges move toward and away from each other as the arms pivot. Disposed between the flanges and limiting the proximity of the flanges to one another to thereby limit the forward movement of the arms is an extension block 63. The extension block is part of the wedge extension stop 10 which is removably mounted on one of the face plates of the polycentric hinge.

As shown in FIGS. 2, 4 and 6, extension stop 10 is C-shaped and includes at one end the extension block 63, a clip 65 at the opposing end, and a connecting member 64 between the extension block 63 and clip 65. Extension block 63 is disposed adjacent the front edge 90 of the hinge between the flanges 61, 62 and between the face plates 51, 52. A shoulder 77 adjacent extension block 63 seats in a complimentary-shaped notch 78 in the front edge of plate 51 to locate and secure extension block 63 in a centered position between flanges 61, 62.

At the opposing end of extension stop 10 is the resilient hook or clip 65 secured to the rear edge 93 of face plate 51. Connecting member 64 extending between extension block 63 and clip 65 lies along the outer surface 67 of face plate 51. The stop 10 is preferably made of a strong, lightweight and resilient plastic such as nylon.

As shown more clearly in FIG. 6, the extension block 63 is a five-sided body. A front side 101 is linear and substantially vertically disposed in the plane of the front surface 90 of the hinge. Opposing top and bottom sides 102 and 103 angle outwardly so as to increase the height of the block in the rearward direction. Curved rear edges 104 and 105 extend between the top and bottom edges in the rearward direction. The block is shaped so that outwardly projecting flanges 61 and 62 on the mating ends 49 and 50 of the arms cause a rearward force on the extension block so as to maintain the block securely on the hinge whether the extension limit is 0° or 40° as hereinafter described.

Figure 8:
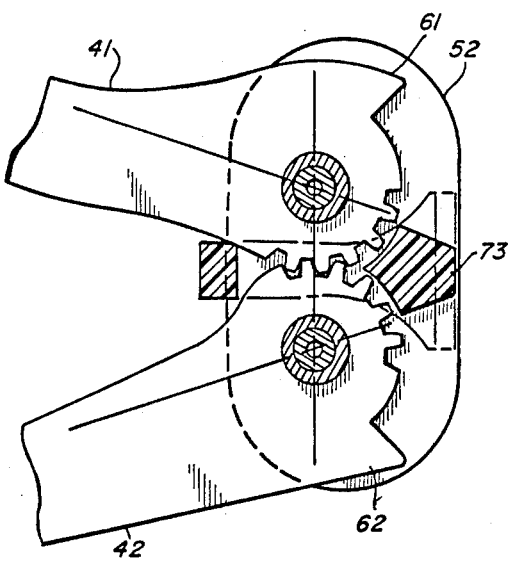
FIG. 8 is a side partially sectional view of the hinge and stop with the arms rotated rearwardly to release the extension block.

One of the principal benefits of the extension stop of this invention is that because it is removable, the user can select an extension stop having any of several different size extension blocks to limit the extension of the arms to any predetermined amount. As shown in FIG. 2, an extension block 63 having a first height (as defined by the length of front side 101) is positioned between the flanges 61, 62 of the rigid arms to limit the movement of each arm to an angle A of 5° from vertical, for a total arm extension of 170°. As shown in FIG. 7, an extension stop 73 having a second height (less than the first height) is positioned between the flanges 61, 62 to allow a full extension of 180° of the arms. As shown in FIG. 9, an extension stop 83 having a third height (greater than the first height) is positioned between flanges 61 and 62 to allow a 100° extension of the arms. Thus, by selecting the dimensions of the block, the user can set the extension limit too, for example, 0° (FIG. 7), 10° (FIG. 2), 20°, 30° or 40° (FIG. 9). As shown in FIG. 8, the extension block 73 is easily removable from between the flanges by rotating the arms rearwardly to a position which relieves any pressure on the extension block.

When using the extension stop of this invention with a knee brace, it is further preferred to provide the apertures on the mating ends 49 and 50 of the arms offset forwardly from the vertical center line of the arms so that the hinged brace better conforms to the geometry of the leg. As shown in FIG. 2, the mating ends of the arms are offset forwardly as well as the apertures through which rivets 53 and 54 extend.

The extension stop is useful in any type of polycentric hinge wherein it is desired to limit the extension of the arms connected by the hinge. The extension stop would be useful in an elbow brace and in any other type of brace to permit limited pivotal movement. There are no tools required to position the extension stop nor any straps to adjust and readjust. The extension stop provides a precise, strong and reliable means for controlling the movement of the polycentric hinge.

Having described a preferred embodiment in detail, those skilled in the art will appreciate that numerous modifications may be made thereof without departing from the spirit of this invention. Therefore, it is not intended that the scope of the invention be limited by the specific embodiment illustrated and described herein but rather it is intended that the scope of the invention be determined by the appended claims and their equivalents.

We claim:

1. A removable extension stop for limiting forward pivotal movement of a pair of arms connected by a polycentric hinge, said polycentric hinge being of the type including a pair of parallel spaced-apart face plates wherein the arms are pivotally secured at mating ends between the face plates at spaced-apart pivotal connections, said hinge having opposing front and rear edges, said mating ends of the arms having intermeshing gear teeth so as to cause simultaneous pivotal movement of the arms about their pivotal connections with the plates, and said mating ends of the arms having a pair of flanges adjacent the front edge of the hinge to limit the forward pivotal movement of the arms when the flanges engage the extension stop, said extension stop comprising a C-shaped body having:
    a clip means at one end of the body positionable adjacent the rear edge of the hinge for releasably securing the body to the hinge,
    an extension block at the opposing end of the body positionable adjacent the front edge of the hinge,
    and a connecting member extending between the clip means and extension block,
    said extension block being positionable between the mating ends of the arms to engage the flanges and limit the forward pivotal movement of the arms toward the front edge of the hinge, and wherein said extension block has a front edge positionable adjacent the front of the hinge and a pair of diverging top and bottom edges extending from the front edge and angled outwardly toward the rear of the hinge such that the flanges cause a rearward pressure on the top and bottom edges of the block to secure the block in position on the hinge.

2. The extension stop of claim 1, wherein said clip means engages the rear edge of one of the face plates.

3. The extension stop of claim 1, wherein said body further includes a shoulder adjacent to the extension block which is shaped to fit within a complimentary shaped notch in one of the face plates.

4. The extension stop of claim 1, wherein said front edge of said extension block is of a predetermined size to provide an extension limit from about 0° to 40°.

5. The extension stop of claim 1, wherein the stop is made of plastic.

6. The extension stop of claim 5, where the connecting member is resilient to permit ready attachment and removal of the stop to the hinge.

7. The extension stop of claim 1 in combination with a knee brace wherein the stop limits the forward pivotal movement of the brace.

8. The combination of claim 1, wherein the pivotal connection between the mating ends of the arms and the face plates are offset forwardly of the center line of the arms.

9. A removable extension stop for limiting the forward pivotal movement of a pair of arms connected by a polycentric hinge, said polycentric hinge being of the type including a pair of parallel spaced-apart face plates wherein the arms are pivotally secured at mating ends between the face plates at spaced-apart pivotal connections, said hinge having opposing front and rear edges, said mating ends of the arms having intermeshing gear teeth so as to cause simultaneous pivotal movement of the arms about their pivotal connections with the plates, said rotating ends of the arms having flanges to limit the forward pivotal movement of the arms when the flanges engage the extension stop, said extension stop comprising:
    means for removably attaching the extension stop to the polycentric hinge; and
    extension block means positionable between the mating ends of the arms to engage the flanges and to limit the forward pivotal movement of the arms, wherein said block means is disposed adjacent the front edge of the hinge and includes a pair of top and bottom edges which diverge outwardly going from the front toward the rear of the hinge so that the flanges exert a rearward pressure on the block means.

* * * * *

UNITED STATES PATENT AND TRADEMARK OFFICE
CERTIFICATE OF CORRECTION

PATENT NO. : 4,732,143

DATED : March 22, 1988

INVENTOR(S) : James Kausek

It is certified that error appears in the above-identified patent and that said Letters Patent is hereby corrected as shown below:

Column 2, line 43, "persepctive" should read -- perspective --.

Column 2, line 49, "hin ge" should read -- hinge --.

Column 3, line 12, "skin" should read -- shin --.

Column 3, line 66, "spacedapart" should read -- spaced-apart --.

Signed and Sealed this

Second Day of August, 1988

Attest:

DONALD J. QUIGG

Attesting Officer

Commissioner of Patents and Trademarks